(12) United States Patent
Mitsui (10) Patent No.: US 9,664,926 B2
(45) Date of Patent: May 30, 2017

(54) CONTACT LENS FOR CORNEA-CORRECTION CROSSLINKING

(71) Applicant: Iwane Mitsui, Tokyo (JP)

(72) Inventor: Iwane Mitsui, Tokyo (JP)

(*) Notice: Subject to any disclaimer, the term of this patent is extended or adjusted under 35 U.S.C. 154(b) by 0 days.

(21) Appl. No.: 14/916,164

(22) PCT Filed: Oct. 7, 2015

(86) PCT No.: PCT/JP2015/078442
§ 371 (c)(1),
(2) Date: Mar. 2, 2016

(87) PCT Pub. No.: WO2016/056575
PCT Pub. Date: Apr. 14, 2016

(65) Prior Publication Data
US 2016/0296368 A1    Oct. 13, 2016

(30) Foreign Application Priority Data

Oct. 10, 2014  (JP) .................. 2014-209471
May 29, 2015  (JP) .................. 2015-110788

(51) Int. Cl.
*A61F 9/007*   (2006.01)
*A61N 5/06*    (2006.01)
(Continued)

(52) U.S. Cl.
CPC .............. *G02C 7/047* (2013.01); *A61F 9/007* (2013.01); *A61F 9/0079* (2013.01); *A61F 9/013* (2013.01);
(Continued)

(58) Field of Classification Search
CPC ........ A61F 9/0079; A61F 9/007; A61F 9/013; A61K 31/525; A61L 27/00; A61N 5/062;
(Continued)

(56) References Cited

U.S. PATENT DOCUMENTS

2010/0318017 A1   12/2010  Lewis et al.
2013/0144260 A1*   6/2013  Dewoolfson ......... A61F 9/0017
                                            604/506
(Continued)

FOREIGN PATENT DOCUMENTS

JP       H07-500267 A   1/1995
JP          3044891 U   1/1998
(Continued)

OTHER PUBLICATIONS

Koppen et al., "Influence of contact lens wear on the results of ultraviolet A/riboflavin cross-linking for progressive keratoconus," Br J Ophthalmol, Jul. 27, 2011, vol. 95, No. 10, pp. 1402-1405.
(Continued)

*Primary Examiner* — Jordan Schwartz
*Assistant Examiner* — George G King
(74) *Attorney, Agent, or Firm* — Oliff PLC (57) ABSTRACT

A contact lens for cornea-correction crosslinking made of an ultraviolet transmitting material includes, on a cornea contact side, a pressing region projecting in a convex curved-surface shape at a position corresponding to the center of a corneal dome to be pressed and a relief region constituted by an annular concave portion in a circular arc shape, encircling the outer periphery of the pressing region. The contact lens corrects at least naked eye vision or keratoconus cornea by pressing both regions to the cornea and changing its shape. The contact lens includes a reservoir portion outside the pressing region in a lens thickness direction for a riboflavin solution, a communication hole communicating the reservoir portion inside with the pressing region, and an operation-side electrode having the same polarity as that of the riboflavin solution. The mounted contact lens allows riboflavin solution infiltration into corneal tissue by iontophoresis and ultra-violet ray irradiation.

16 Claims, 4 Drawing Sheets

(51) Int. Cl.
G02C 7/04 (2006.01)
A61L 27/00 (2006.01)
A61F 9/013 (2006.01)
A61K 31/525 (2006.01)

(52) U.S. Cl.
CPC ............ *A61K 31/525* (2013.01); *A61L 27/00* (2013.01); *A61N 5/062* (2013.01); *G02C 7/04* (2013.01); *A61N 2005/0661* (2013.01)

(58) Field of Classification Search
CPC . A61N 2005/0661; G02C 7/0047; G02C 7/04
USPC ......................................... 351/159.23; 606/5
See application file for complete search history.

(56) References Cited

U.S. PATENT DOCUMENTS

2014/0379054 A1* 12/2014 Cooper ................. A61F 9/0079
607/90

2015/0374540 A1* 12/2015 Lopath ................... A61F 9/008
606/5

FOREIGN PATENT DOCUMENTS

| JP | H11-244323 A | 9/1999 |
| JP | 2003-144479 A | 5/2003 |
| JP | 2012-502668 A | 2/2012 |
| JP | 2013-066624 A | 4/2013 |
| JP | 2013-521988 A | 6/2013 |
| JP | 2014-503317 A | 2/2014 |
| JP | 2015-036080 A | 2/2015 |
| WO | 9307840 A1 | 4/1993 |
| WO | 2009/090763 A1 | 7/2009 |

OTHER PUBLICATIONS

Translation of Dec. 8, 2015 Written Opinion of the International Searching Authority issued in International Patent Application No. PCT/JP2015/078442.

* cited by examiner

FIG. 6

CONTACT LENS FOR CORNEA-CORRECTION CROSSLINKING

TECHNICAL FIELD

The present invention relates to a contact lens for cornea-correction crosslinking that changes a shape of the cornea of a patient while being mounted for a given period of time, and allows, in a state of correcting myopia, hyperopia, or keratoconus cornea, infiltration of a riboflavin (vitamin B2) solution into a corneal tissue and ultra-violet ray irradiation for crosslinking collagens constituting the cornea to one another, thereby enhancing strength of the cornea and fixing thereof.

BACKGROUND ART

There has been developed a contact lens for changing the shape of the cornea of a patient by being mounted during sleep and the like, and correcting myopia, hyperopia, and/or astigmatism at the time when the contact lens is removed.

When the above-described contact lens is not put on for a long period, myopia or hyperopia is returned to its original condition by a restoring force of the cornea, thus it is desirable for the cornea to be fixed in a corrected state.

On the other hand, there has been known a refraction correction surgery in which a corneal tissue in a state of being infiltrated with riboflavin (vitamin B2) is irradiated with ultra-violet rays for crosslinking collagens constituting the cornea to one another, thereby enhancing strength of the cornea and fixing the cornea.

For crosslinking the cornea, while opening the eye of a patient, a riboflavin solution is dropped from a cylindrical reservoir unit mounted on the cornea so as to be infiltrated into the cornea.

Further, in Patent Literature 1, the present inventor proposed a contact lens for cornea-correction crosslinking and a cornea-correction crosslinking method.

This method is intended to fix the shape of a cornea to some extent in a state of being corrected by a contact lens by combining a crosslinking method and a cornea-correction contact lens.

Also in this case, as the above-mentioned method, infiltration of a riboflavin solution is performed with the cornea-correction contact lens being removed.

As such, when a riboflavin solution is dropped for infiltration while the eye of a patient being opened, there are such problems that the patient is restrained in a state of opening the eye for a long time (about 30 minutes), and since not all dropped riboflavin solution infiltrates into the cornea and most of it leaks outside, a physician needs to frequently carry out a task of absorbing the leaked riboflavin solution. Furthermore, when ultra-violet ray irradiation is performed, a contact lens is mounted after a riboflavin solution infiltrates into the cornea, thus there is such a problem that deformation characteristic of the cornea becomes different from that before infiltration of the riboflavin solution, making it impossible to sufficiently correct the cornea.

CITATION LIST

Patent Literature

Patent Literature 1: Japanese Patent Application Laid-Open No. 2015-36080

SUMMARY OF INVENTION

Technical Problem

An object of the present invention is to provide a contact lens for cornea-correction crosslinking that allows, while being mounted on a patient, infiltration of a riboflavin solution into the cornea in a short time and ultraviolet-ray irradiation for crosslinking the cornea.

Solution to Problem

It has been found that, by providing a contact lens for cornea-correction crosslinking with a reservoir portion capable of storing a riboflavin solution for cornea-correction crosslinking, an operation-side electrode having the same polarity as that of the riboflavin solution, the electrode being provided at a position in contact with the riboflavin solution in the reservoir portion, and a communication hole for guiding the riboflavin solution in the reservoir portion to the inside of the lens, the riboflavin solution can be infiltrated quickly and surely by iontophoresis and also ultraviolet-rays can be irradiated while the contact lens remains mounted on the cornea, that is, in a state in which the cornea is being corrected.

In summary, the above-described objectives are achieved by the following embodiments of the present invention.

(1) A contact lens for cornea-correction crosslinking made of an ultraviolet transmitting material, the contact lens having a relief region constituted by a concave portion and a pressing region constituted by a convex region being formed on a side of the contact lens in contact with a cornea of a patient, the contact lens being for correcting at least one of naked eye vision and keratoconus cornea by pressing the relief region and the pressing region to the cornea and changing a shape of the cornea, wherein, when the contact lens is mounted on the cornea, the pressing region is projected in a convex curved-surface shape at a position corresponding to a center of a corneal dome to be pressed, thereby forming a concave curved-surface on the cornea; the relief region is constituted by an annular concave portion that has a cross section in a concave circular arc shape and is formed at a position encircling an outer periphery of the pressing region, and the contact lens further comprises: an anchor region provided at a position encircling an outer periphery of the relief region, the anchor region having a shape aligned with a contour of the cornea when the contact lens is mounted on the cornea; a peripheral portion encircling an outer periphery of the anchor region; a reservoir portion for storing a riboflavin solution for cornea-correction crosslinking, the reservoir portion being provided outside the pressing region in a thickness direction of the contact lens; a communication hole for communicating an inside of the reservoir portion with the pressing region, and an operation-side electrode having a same polarity as that of the riboflavin solution, the operation-side electrode being provided at a position in contact with the riboflavin solution in the reservoir portion, thereby allowing infiltration of the riboflavin solution into a corneal tissue by iontophoresis.

(2) A contact lens for cornea-correction crosslinking made of an ultraviolet transmitting material, the contact lens having a relief region constituted by a concave portion and a pressing region constituted by a convex region being formed on a side of the contact lens in contact with a cornea of a patient, the contact lens being for correcting at least one of naked eye vision and keratoconus cornea by pressing the relief region and the pressing region to the cornea and changing a shape of the cornea, wherein, when the contact lens is mounted on the cornea, the relief region is formed in a concave curved-surface shape at a position corresponding to a center of a corneal dome to be in contact with, thereby forming a convex curved-surface on the cornea, the pressing region is constituted by an annular convex portion that has a cross section in a convex circular arc shape and is formed at a position encircling an outer periphery of the relief region; and the contact lens further comprises: an anchor region provided at a position encircling an outer periphery of the pressing region, the anchor region having a shape aligned with a contour of the cornea when the contact lens is mounted on the cornea; a peripheral portion encircling an outer periphery of the anchor region; a reservoir portion for storing a riboflavin solution for cornea-correction crosslinking, the reservoir portion being provided outside the relief region in a thickness direction of the contact lens; a communication hole for communicating an inside of the reservoir portion with the relief region; and an operation-side electrode having a same polarity as that of the riboflavin solution, the operation-side electrode being provided at a position in contact with the riboflavin solution in the reservoir portion, thereby allowing infiltration of the riboflavin solution into a corneal tissue by iontophoresis.

Advantageous Effects of Invention

With the contact lens for cornea-correction crosslinking according to the present invention, a riboflavin solution can be surely infiltrated into the cornea of a patient in a short time while the contact lens remains mounted on the cornea, that is, in a state in which the cornea is being corrected.

DESCRIPTION OF EMBODIMENTS

An embodiment of the present invention will be explained.

In the contact lens for cornea-correction crosslinking according to the present embodiment, a relief region constituted by a concave portion and a pressing region constituted by a convex portion are formed on a side of the lens in contact with the cornea of a patient. By pressing the relief region and the pressing region to the cornea, a part of the cornea is pushed downward and, as a reaction thereof, a part of the cornea is projected into the relief region, so that the cornea is corrected into a shape in which desirable naked eye vision can be obtained or a shape in which keratoconus cornea is smoothly suppressed. When the contact lens is removed after corneal deformation is fixed by crosslinking in this state, a return of corneal deformation occurs due to spring back of the eyeball (elongation of ocular axial length). Thus a curvature of the curve of the convex portion or the concave portion is set anticipating this return. Under such a setting, a riboflavin solution in a reservoir portion is allowed to infiltrate into the cornea from the outside of the contact lens via a communication hole provided so as to penetrate the contact lens by an action of iontophoresis, and also the cornea is irradiated with ultra-violet rays via the contact lens after infiltration.

An operation-side electrode has the same polarity as that of the riboflavin solution, thus when a DC current is applied, the riboflavin solution is repelled from the operation-side electrode, and also sucked by a non-operation-side electrode, resulting in infiltrating into the cornea.

It is noted that the present invention is also applied to the case where a return of corneal deformation due to spring back of the eyeball (elastically restoring force) is not anticipated.

In an actual treatment, a contact lens is changed stepwise so as to correct eyesight to a desired level. At a final step, while using a contact lens that forms a concave curved-surface having a curvature of $R_0$ on the cornea for obtaining desired eyesight, the riboflavin solution is allowed to infiltrate and, ultra-violet rays are irradiated to the cornea via the contact lens while that state is maintained.

When elastically restoring force of the eyeball is not considered, the above-described concave curved-surface of curvature $R_0$ is formed by the pressing region having the convex curved-surface of curvature $R_0$.

A feature of the present embodiment is that, in case of correcting myopia, when a curvature of the concave curved-surface to be formed on the cornea is defined as $R_0$ and a curvature of the convex curved-surface of the pressing region is defined as $R_s$, $R_s$ is set to satisfy $R_s=R_0+5.0$ D to $R_0+10.0$ D.

In this formula, D represents diopter as a unit for indicating refractivity of the eye. The above-mentioned values from +5.0 D to +10.0 D are a correction amount obtained by taking into consideration corneal deformation based on elastically restoring force of the eyeball after crosslinking, and deduced from a large number of treatment cases performed by the inventor. It is noted that it was not conventionally known that corneal deformation after crosslinking is caused by elastically restoring force of the eyeball until the inventor has found it.

The above-mentioned values are determined as follows: when the cornea of a patient is pressed by the pressing region having the convex curved-surface of curvature $R_0$ and then the pressing is released, provided that a curvature variation at the central area of a corneal dome due to elastically restoring force of the eyeball is defined as $\Delta R$, the curvature $R_s$ is obtained by $R_s=R_0+\Delta R$.

Furthermore, another feature of the present embodiment is that, in case of correcting hyperopia, the pressing region and the relief region are reversed to each other as compared to the case of correcting myopia, and when a curvature of the convex curved-surface to be formed on the cornea is defined as $r_0$ and a curvature of the concave curved-surface of the relief region is defined as $r_s$, $r_s$ is set to satisfy $r_s=r_0-6.5$ D to $r_0$–11.5 D. Also in this formula, the above-mentioned values of –6.5 D to –11.5 D are deduced from treatment cases.

Also in the case of correcting hyperopia, the above-mentioned values are based on the fact that, when a curvature variation at the central area of the corneal dome due to elastically restoring force of the eyeball is defined as Δr, the curvature $r_s$ is obtained by $r_s = r_0 - \Delta r$.

Further, it is preferred that, in the contact lens for cornea-correction crosslinking, the outer diameter $D_1$ of a peripheral portion be set larger than the average outer diameter $D_0$ of the outer periphery of the human cornea by 3.0 mm to 5.0 mm, and a UV-shielding membrane for shielding UV rays is provided to the lens in an annular region, on a side in contact with the cornea, from a position having a diameter of $D_0$-3.0 mm to $D_0$-5.0 mm to the outermost periphery in the outer peripheral portion.

When the outer periphery of the cornea (corneal limbus) where pluripotent cells lie is crosslinked by ultra-violet ray irradiation during crosslinking, it becomes difficult to regenerate the cornea. The UV-shielding membrane prevents this from occurring.

As a material of the UV-shielding membrane for shielding ultraviolet rays, a material harmless to the cornea, for example, a gold thin film, a titanium thin film, a silver thin film, and the like may be used.

When the UV-shielding membrane is provided outside the contact lens, ultra-violet rays incident from the central area of the contact lens are reflected/diffracted inside and sometimes reach the outer periphery of the cornea. Thus the UV-shielding membrane is provided on a side in contact with the cornea.

Example 1

Figure 1:
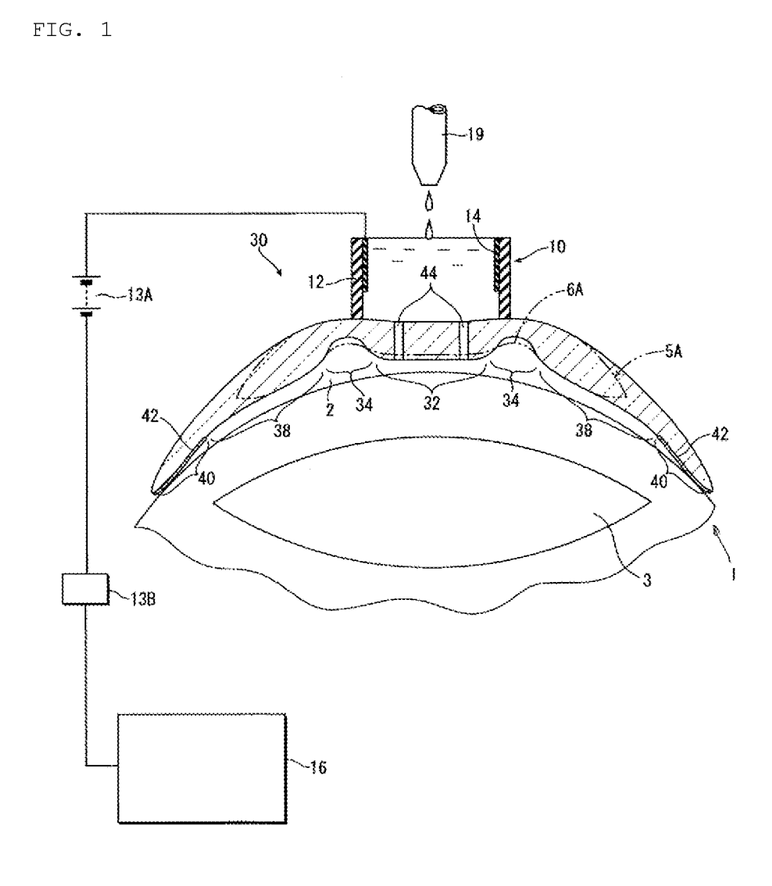
FIG. 1 is a cross-sectional view schematically illustrating a contact lens for cornea-correction crosslinking for correcting myopia according to Example 1 of the present invention.

As shown in FIG. 1, a contact lens for cornea-correction crosslinking (hereinafter referred to as a contact lens) 30 for correcting myopia according to Example 1 of the present invention is used by being mounted on a cornea 2.

The contact lens 30 is configured to include: a pressing region 32 formed to project in a convex curved-surface shape at a position corresponding to the center of a corneal dome (a front end surface of the cornea 2 having the most protruding portion) to be pressed; a relief region 34 constituted by an annular concave portion having a cross section in a concave circular arc shape, the relief region 34 being formed at a position encircling the outer periphery of the pressing region 32; an anchor region 38 having a shape aligned with a contour 36 (see FIG. 2) of the cornea 2 when the contact lens is mounted on the cornea 2, the anchor region 38 being provided at a position encircling the outer periphery of the relief region 34; and a peripheral portion 40 encircling the outer periphery of the anchor region 38.

A reservoir portion 12 is composed of a material that is not liberated in a riboflavin solution even when a current is allowed to flow, and an operation-side electrode 14 is composed of a strip-shaped conductive material such as a gold thin film or a conductive resin, formed in a cylindrical shape on the inner peripheral surface of the reservoir portion 12.

A non-operation-side electrode 16 is composed of a conductive rubber, for example, and adhered to the skin of a human body by a conductive adhesive, allowing the passage of a current.

The operation-side electrode 14 has the same polarity as that of the riboflavin solution. Cation is used in Example.

It is noted that the cornea 2 is shown in a state of being corrected by the contact lens 30.

A cornea infiltration device 10 is provided on the outside (the opposite side of an eyeball 1) of the contact lens 30.

The cornea infiltration device 10 is configured to include: the cylindrical reservoir portion 12 disposed outside of the contact lens 30 so as to correspond to the central area of the cornea 2 of the eyeball 1 of a patient; the operation-side electrode 14 formed on the inner peripheral surface of the reservoir portion 12; the non-operation-side electrode 16 adhered to the skin of the patient in the vicinity of the eyeball 1; and a battery 13A and a switch 13B disposed between the operation-side electrode 14 and the non-operation-side electrode 16.

Reference numerals 3 and 19 in FIG. 1 denote the crystalline lens and a syringe for dropping a riboflavin solution from above the reservoir portion 12, respectively.

A tip (a lower end in FIG. 1) of the cylindrical reservoir portion 12 is connected and mounted on the outside of the contact lens 30.

Figure 2:
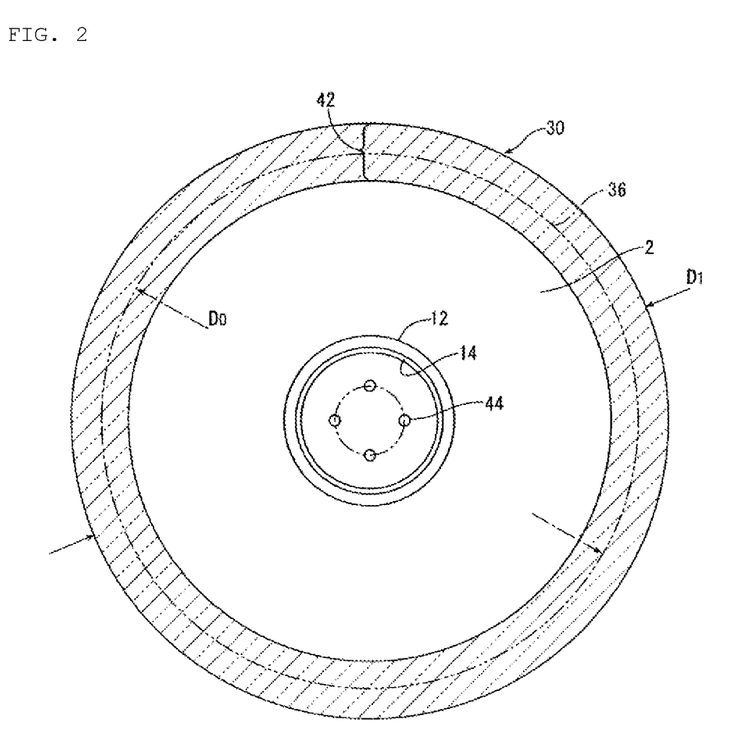
FIG. 2 is a plan view schematically illustrating the contact lens for cornea-correction crosslinking for correcting myopia.

As shown in FIG. 2, communication holes 44 for communicating the inside of the reservoir portion 12 with the pressing region 32 are provided to the contact lens 30 on the same virtual circle encircling the center of the contact lens 30 (a lens center) at equal intervals (equal angular intervals of 45° C.) at four points so as to penetrate the pressing region 32 in a thickness direction of the lens.

An inner diameter of the reservoir portion 12 is sized so as to surround the four communication holes 44 and the outer periphery of the pressing region 32. In FIG. 1, a conventional contact lens (hereinafter referred to as a conventional lens) 5A for correcting myopia is shown by a two-dot chain line. This conventional contact lens 5A for correcting myopia includes a pressing region (with a convex curved-surface of curvature $R_0$) for forming a concave curved-surface of curvature $R_0$ in order to obtain a targeted naked eye vision of a patient.

In the contact lens 30 according to Example 1, as shown by a solid line in FIG. 1, the pressing region 32 is projected towards a direction of the cornea 2 in contrast to the conventional lens 5A, and conversely the relief region 34 forms a deeper annular concave portion than a relief region 6A of the conventional lens 5A. Furthermore, the peripheral portion 40 is larger than a peripheral portion of the conventional lens 5A and extended along the contour 36 of the cornea 2.

In this configuration, when a curvature of the convex curved-surface of the pressing region 32 in Example 1 is defined as $R_s$ and a curvature of the convex curved-surface of the conventional lens 5A is defined as $R_0$, $R_s$ is set to satisfy $R_s = R_0 + 5.0$ D to $R_0 + 10.0$ D.

The aforementioned curvature $R_0$ is a curvature of a concave curved-surface to be formed on the cornea 2 for correcting at least one of naked eye vision and keratoconus cornea of a patient. The reason $R_s$ is set to satisfy $R_s > R_0$ is that when the cornea of a patient is pressed by the pressing region having a convex curved-surface of curvature $R_0$ and then the pressing is released, the cornea is deformed so as to lessen a curvature of the concave curved-surface at the central area of the corneal dome due to elastically restoring force (spring back) of the eyeball, thus $R_s$ is set anticipating this spring back amount. As a result, when this spring back amount is defined as ΔR, the curvature $R_s$ is obtained by $R_s = R_0 + \Delta R$.

Specifically, the spring back amount varies by patient and ΔR is obtained by trial-and-error, however it was found, from treatment cases, that this could be solved by setting $R_s$ to generally satisfy $R_s=R_0+5.0$ D to $R_0+10.0$ D.

As shown in FIG. 1 and FIG. 2, an outer diameter $D_1$ of the peripheral portion 40 of the contact lens 30 is set larger than an average outer diameter $D_0$ of the outer peripheral edge of the human cornea by 3.0 mm to 5.0 mm, and a UV-shielding membrane 42 for shielding ultraviolet rays is provided to the lens in an annular region, on a side in contact with the cornea, from a position having a diameter of $D_0$-3.0 mm to $D_0$-5.0 mm to the outermost periphery in the peripheral portion 40. The UV-shielding membrane 42 is preferably made of a material that is harmless even when being in contact with the cornea 2, including, for example, a thin film of gold, titanium, silver, and the like.

As shown in FIG. 2, when the UV-shielding membrane 42 is formed, the peripheral portion 40 of the cornea 2 is not damaged by ultra-violet ray irradiation during crosslinking, thus pluripotent cells for regenerating the cornea can be preserved.

A description will next be given of a process for fixing the cornea 2 by crosslinking in a state in which the cornea 2 is corrected using the contact lens 30.

First, the contact lens 30 having the cornea infiltration device 10 attached to the outside of the contact lens is mounted on the cornea 2 of a patient, and the cornea 2 is corrected along the shapes of the pressing region 32 and the relief region 34 located inside the contact lens 30.

Next, while keeping the above-mentioned corrected state, without removing the contact lens 30, a riboflavin solution is injected into the reservoir portion 12, and subsequently, a current is supplied between the operation-side electrode 14 and the non-operation-side electrode 16 from the battery 13A.

Since the riboflavin solution has the same polarity as that of the operation-side electrode 14, the riboflavin solution is repelled and moves in a direction of the non-operation-side electrode 16, that is, a direction of the cornea 2 by the action of iontophoresis.

During this process, since the communication holes 44 are formed between the reservoir portion 12 and a surface of the cornea 2, the riboflavin solution in the reservoir portion 12 readily reaches the surface of the cornea 2 through the communication holes 44, and then infiltrates into the cornea 2.

After the cornea 2 is infiltrated with the riboflavin solution, the cornea 2 is irradiated with ultra-violet rays in this state via the contact lens 30, thereby crosslinking collagen fibers that constitute the cornea 2.

During this process, since the reservoir portion 12 is formed in a hollow cylindrical shape, ultra-violet ray irradiation can be performed even when the reservoir portion 12 remains attached to the contact lens 30.

The UV-shielding membrane 42 is formed on the contact lens 30 on a side in contact with the cornea 2 so as to cover the peripheral portion 40, thus ultra-violet rays do not reach the cornea 2. Thus, pluripotent cells of the cornea 2, localized inside the peripheral portion 40, are not damaged.

Further, even when the contact lens 30 is removed after completion of the ultra-violet ray irradiation, the cornea 2 is fixed in the same shape as conferred by the pressing region 32 and the relief region 34.

After the contact lens 30 is removed, the central area of the cornea 2 is projected due to elastically restoring force of the eyeball. However since the curvature $R_s$ of the convex curved-surface of the pressing region 32 is set anticipating the spring back amount in advance, a curvature of the concave curved-surface formed on the cornea 2 comes to $R_0$ after spring back.

Example 2

Figure 3:
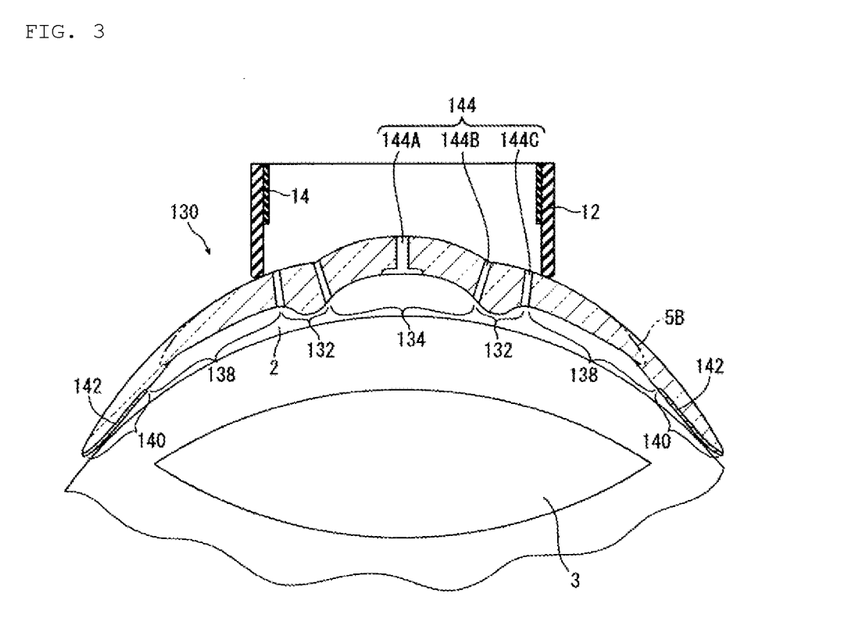
FIG. 3 is a cross-sectional view schematically illustrating a contact lens for cornea-correction crosslinking for correcting hyperopia according to Example 2 of the present invention.

Next, a contact lens 130 for correcting hyperopia according to Example 2, shown in FIG. 3, will be described. In FIG. 3, a conventional contact lens 5B for correcting hyperopia is shown by a two-dot chain line.

The contact lens 130 for correcting hyperopia according to Example 2 has a configuration in which a concave part and a convex part are switched between the pressing region and the relief region as compared to the contact lens 30 shown above in FIG. 1.

In the contact lens 130 for correcting hyperopia, a relief region 134 is formed in a concave curved-surface shape at a position corresponding to the central area of a corneal dome to be in contact with when the lens 130 is mounted on the cornea 2, and a pressing region 132 is constituted by an annular convex portion having a cross section in a convex circular arc shape and formed at a position encircling the outer periphery of the relief region 134.

Furthermore, an anchor region 138 is provided at a position encircling the outer periphery of the pressing region 132 and formed into a shape aligned with a contour 136 (see FIG. 4) of the cornea when the lens 130 is mounted on the cornea 2. A peripheral portion 140 is configured so as to encircle the outer periphery of the anchor region 138. Reference numeral 142 in FIG. 3 denotes a UV-shielding membrane.

In the contact lens 130 for correcting hyperopia according to Example 2, a total of nine communication holes 144 penetrating the contact lens 130 for correcting hyperopia in a thickness direction thereof are formed between the inside of the reservoir portion 12 and the cornea 2 surface.

Figure 4:
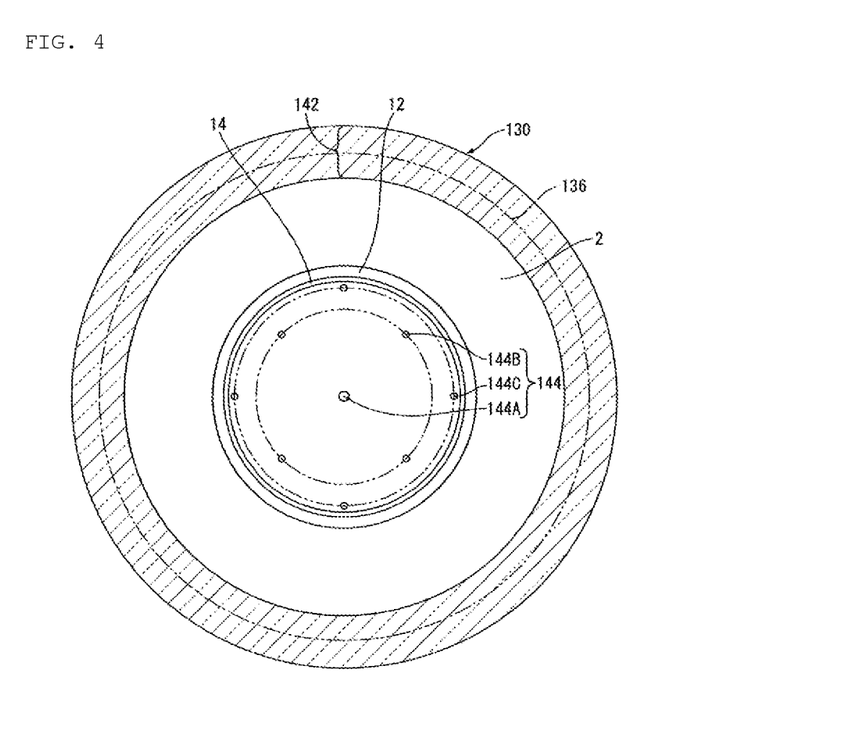
FIG. 4 is a plan view schematically illustrating the contact lens for cornea-correction crosslinking for correcting hyperopia.

A central communication hole 144A having a larger inner diameter is provided at the central position of the contact lens 130 for correcting hyperopia, and four intermediate communication holes 144B and four outside communication holes 144C are formed on two concentric circles surrounding the central communication hole 144A, respectively (see FIG. 4). The intermediate communication holes 144B are provided inside the relief region 134, at positions adjacent to the lens center side of the pressing region 132, and the outside communication holes 144C are provided at positions adjacent to a side (the outside) opposite to the lens center of the pressing region 132.

Both the intermediate communication holes 144B and the outside communication holes 144C may be provided at a plurality of, three or more, points at equal intervals. Further, when the intermediate communication holes 144B are provided inside the pressing region 132, the outside communication holes 144C may not be provided.

Further, in the contact lens 130 for correcting hyperopia according to Example 2, when a curvature of the convex curved-surface to be formed on the cornea 2 for vision correction is defined as $r_0$ and a curvature of the concave curved-surface of the relief region 134 is defined as $r_s$, $r_s$ is set to satisfy $r_s=r_0-6.5$ D to $r_0-11.5$ D.

The value is a correction amount obtained by taking into consideration a spring back amount $\Delta r$ due to elastically restoring force of the eyeball at the central area of the corneal dome after releasing the pressing force of the contact lens 130 for correcting hyperopia, deduced from a large number of treatment cases performed by the inventor. The curvature $r_s$ is obtained by $r_s=r_0-\Delta r$.

When crosslinking is performed to the corrected cornea using the contact lens 130 for correcting hyperopia, crosslinking is performed through the same process as for the contact lens 30 for correcting myopia according to the aforementioned Example 1.

Example 3

Figure 5:
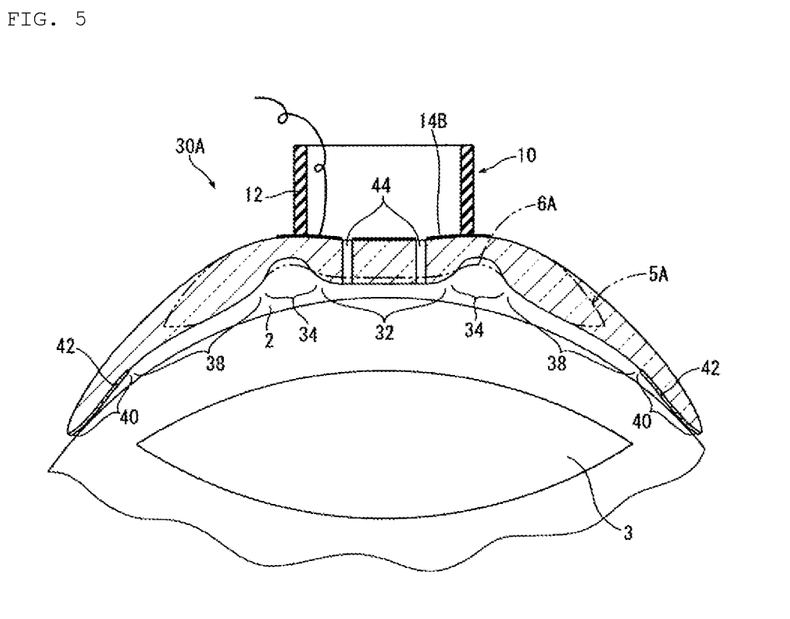
FIG. 5 is a cross-sectional view schematically illustrating a contact lens for cornea-correction crosslinking for correcting myopia according to Example 3 of the present invention.

A contact lens for cornea-correction crosslinking 30A for correcting myopia according to Example 3, shown in FIG. 5, is a modified example of the contact lens 30 according to Example 1 and provided with, for example, a light-transmitting conductive film or a light-transmitting metal thin film to serve as an operation-side electrode 14B on the lens surface that is in contact with the reservoir portion 12.

Example 4

Figure 6:
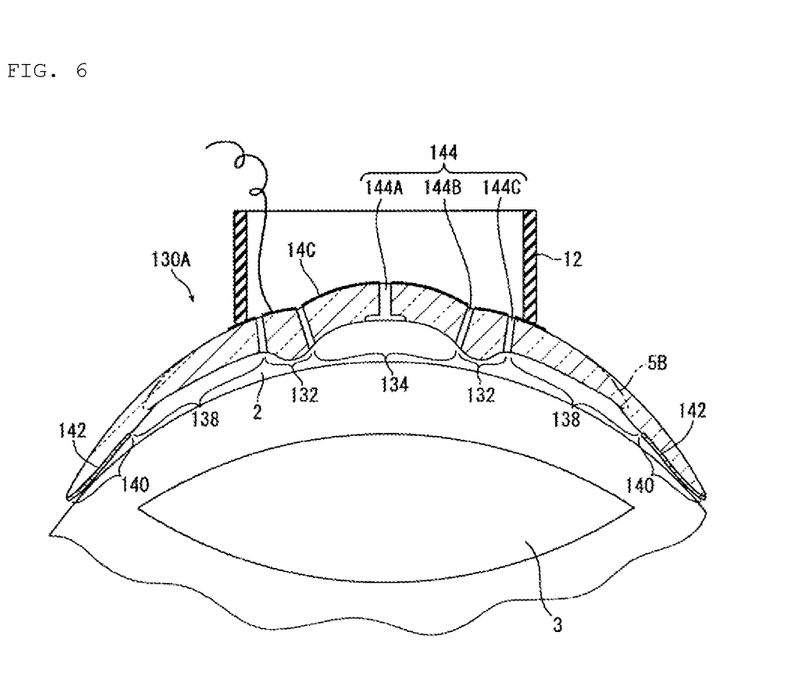
FIG. 6 is a cross-sectional view schematically illustrating a contact lens for cornea-correction crosslinking for correcting hyperopia according to Example 4 of the present invention.

A contact lens for cornea-correction crosslinking 130A for correcting hyperopia according to Example 4, shown in FIG. 6, is a modified example of the contact lens 130 for correcting hyperopia according to Example 2 and provided with, for example, a light-transmitting conductive film or a light-transmitting metal thin film to serve as an operation-side electrode 14C on the lens surface that is in contact with the reservoir portion 12.

INDUSTRIAL APPLICABILITY

The present invention can be used as a contact lens for cornea-correction crosslinking, allowing quick and sure infiltration of a riboflavin solution when the cornea is fixed by crosslinking in a state in which a shape of the cornea is corrected by the contact lens.

REFERENCE SIGNS LIST

1 . . . eyeball
2 . . . cornea
3 . . . crystalline lens
10 . . . cornea infiltration device
12 . . . reservoir portion
13A . . . battery
13B . . . switch
14 . . . operation-side electrode
16 . . . non-operation-side electrode
19 . . . syringe
30, 130, 130A . . . cornea-correction crosslinking contact lens (contact lens)
32, 132 . . . pressing region
34, 134 . . . relief region
36, 136 . . . contour
38, 138 . . . anchor region
40, 140 . . . peripheral portion
42, 142 . . . UV-shielding membrane
44, 144 . . . communication holes
144A . . . central communication hole
144B . . . intermediate communication holes
144C . . . outside communication holes

The invention claimed is:

1. A contact lens for cornea-correction crosslinking comprising an ultraviolet transmitting material, the contact lens having a relief region constituted by a concave portion and a pressing region constituted by a convex region being formed on a side of the contact lens in contact with a cornea of a patient, the contact lens being for correcting at least one of naked eye vision and keratoconus cornea by pressing the pressing region to the cornea and changing a shape of the cornea, wherein,
when the contact lens is mounted on the cornea, the pressing region is projected in a convex curved-surface shape at a position corresponding to a center of a corneal dome to be pressed, thereby forming a concave curved-surface on the cornea;
the relief region is constituted by an annular concave portion that is not in contact with the cornea when the contact lens is mounted on the cornea and that has a cross section in a concave circular arc shape and is formed at a position encircling an outer periphery of the pressing region, and
the contact lens further comprises:
an anchor region provided at a position encircling an outer periphery of the relief region, the anchor region having a shape aligned with a contour of the cornea when the contact lens is mounted on the cornea;
a peripheral portion encircling an outer periphery of the anchor region;
a reservoir portion for storing a riboflavin solution for cornea-correction crosslinking, the reservoir portion being centrally located and being provided outside the pressing region in a thickness direction of the contact lens;
at least one communication hole for communicating an inside of the reservoir portion with the pressing region, and
an operation-side electrode having a same polarity as that of the riboflavin solution, the operation-side electrode being provided at a position in contact with the riboflavin solution in the reservoir portion, thereby allowing infiltration of the riboflavin solution into a corneal tissue by iontophoresis.

2. The contact lens for cornea-correction crosslinking according to claim 1, further comprising a plurality of communication holes, wherein the communication holes are provided so as to penetrate in a thickness direction of the lens at a plurality of points on a same virtual circle encircling a lens center in the pressing region.

3. The contact lens for cornea-correction crosslinking according to claim 2, wherein the communication holes are provided on the same virtual circle at equal angular intervals.

4. A contact lens for cornea-correction crosslinking comprising an ultraviolet transmitting material, the contact lens having a relief region constituted by a concave portion and a pressing region constituted by a convex region being formed on a side of the contact lens in contact with a cornea of a patient, the contact lens being for correcting at least one of naked eye vision and keratoconus cornea by pressing the pressing region to the cornea and changing a shape of the cornea, wherein,
when the contact lens is mounted on the cornea, the relief region is formed in a concave curved-surface shape at a position corresponding to a center of a corneal dome to be in contact with, thereby forming a convex curved-surface on the cornea,
the pressing region is in contact with the cornea when the contact lens is mounted on the cornea and is constituted by an annular convex portion that has a cross section in a convex circular arc shape and is formed at a position encircling an outer periphery of the relief region; and
the contact lens further comprises:
an anchor region provided at a position encircling an outer periphery of the pressing region, the anchor region having a shape aligned with a contour of the cornea when the contact lens is mounted on the cornea;

a peripheral portion encircling an outer periphery of the anchor region;

a reservoir portion for storing a riboflavin solution for cornea-correction crosslinking, the reservoir portion being centrally located and being provided outside the relief region in a thickness direction of the contact lens;

at least one communication hole for communicating an inside of the reservoir portion with the relief region; and an operation-side electrode having a same polarity as that of the riboflavin solution, the operation-side electrode being provided at a position in contact with the riboflavin solution in the reservoir portion, thereby allowing infiltration of the riboflavin solution into a corneal tissue by iontophoresis.

5. The contact lens for cornea-correction crosslinking according to claim 4, further comprising a plurality of communication holes, wherein one of the communication holes is provided at a position of a lens center and a plurality of the communication holes are provided on at least one same virtual circle encircling the lens center at equal angular intervals.

6. The contact lens for cornea-correction crosslinking according to claim 5, wherein the communication holes are provided in the relief region on a virtual circle at a position of the pressing region adjacent to a side closer to the lens center.

7. The contact lens for cornea-correction crosslinking according to claim 4, further comprises an outside communication hole communicating an inside of the reservoir portion with an outer peripheral position of the pressing region.

8. The contact lens for cornea-correction crosslinking according to claim 1, wherein a light-transmitting conductive film or a light-transmitting metal thin film is provided on a lens surface being in contact with the reservoir portion as the operation-side electrode.

9. The contact lens for cornea-correction crosslinking according to claim 7, wherein a light-transmitting conductive film or a light-transmitting metal thin film is provided on a lens surface being in contact with the reservoir portion as the operation-side electrode.

10. The contact lens for cornea-correction crosslinking according to claim 5, further comprises an outside communication hole communicating an inside of the reservoir portion with an outer peripheral position of the pressing region.

11. The contact lens for cornea-correction crosslinking according to claim 6, further comprises an outside communication hole communicating an inside of the reservoir portion with an outer peripheral position of the pressing region.

12. The contact lens for cornea-correction crosslinking according to claim 2, wherein a light-transmitting conductive film or a light-transmitting metal thin film is provided on a lens surface being in contact with the reservoir portion as the operation-side electrode.

13. The contact lens for cornea-correction crosslinking according to claim 3, wherein a light-transmitting conductive film or a light-transmitting metal thin film is provided on a lens surface being in contact with the reservoir portion as the operation-side electrode.

14. The contact lens for cornea-correction crosslinking according to claim 4, wherein a light-transmitting conductive film or a light-transmitting metal thin film is provided on a lens surface being in contact with the reservoir portion as the operation-side electrode.

15. The contact lens for cornea-correction crosslinking according to claim 5, wherein a light-transmitting conductive film or a light-transmitting metal thin film is provided on a lens surface being in contact with the reservoir portion as the operation-side electrode.

16. The contact lens for cornea-correction crosslinking according to claim 6, wherein a light-transmitting conductive film or a light-transmitting metal thin film is provided on a lens surface being in contact with the reservoir portion as the operation-side electrode.

* * * * *